United States Patent
Mouridsen et al.

(10) Patent No.: US 9,679,378 B2
(45) Date of Patent: Jun. 13, 2017

(54) RISK PREDICTION OF TISSUE INFARCTION

(71) Applicant: Aarhus Universitet, Aarhus C (DK)

(72) Inventors: Kim Mouridsen, Hjortshøj (DK); Kartheeban Nagenthiraja, Aarhus N (DK); Mikkel Bo Hansen, Skanderborg (DK)

(73) Assignee: Aarhus Universitet, Aarhus C (DK)

( * ) Notice: Subject to any disclaimer, the term of this patent is extended or adjusted under 35 U.S.C. 154(b) by 25 days.

(21) Appl. No.: 14/428,829

(22) PCT Filed: Sep. 19, 2013

(86) PCT No.: PCT/DK2013/050301
§ 371 (c)(1),
(2) Date: Mar. 17, 2015

(87) PCT Pub. No.: WO2014/044284
PCT Pub. Date: Mar. 27, 2014

(65) Prior Publication Data
US 2015/0228076 A1    Aug. 13, 2015

(30) Foreign Application Priority Data
Sep. 19, 2012   (DK) .................................. 2012 70578

(51) Int. Cl.
*G06K 9/00*    (2006.01)
*G06T 7/00*    (2017.01)
(Continued)

(52) U.S. Cl.
CPC ............ *G06T 7/0014* (2013.01); *G01C 11/04* (2013.01); *G06F 17/18* (2013.01);
(Continued)

(58) Field of Classification Search
CPC ................ G06T 7/00; A61B 5/00; G06K 9/00
(Continued)

(56) References Cited

U.S. PATENT DOCUMENTS 6,662,185 B1 *  12/2003  Stark ........................ A01G 7/00
7,904,135 B2 *  3/2011   Menezes .......... G01R 33/56341
                                                           600/410

FOREIGN PATENT DOCUMENTS

EP    1 255 484 B1      8/2009
WO    WO 01/56466 A2    8/2001

OTHER PUBLICATIONS

Gröschel, Klaus et al., "A risk score to predict ischemic lesions after protected carotid artery stenting" Journal of the Neurological Sciences, 2008, pp. 112-115, vol. 273.
(Continued)

*Primary Examiner* — Abolfazl Tabatabai
(74) *Attorney, Agent, or Firm* — Knobbe, Martens, Olson & Bear, LLP

(57) ABSTRACT

The present invention relates to a method for generating a risk map indicating predicted voxel-by-voxel probability of tissue infarction for a set of voxels, the method comprising the steps of, receiving for each voxel a first value (x) corresponding to a set of tissue marker values and generating the risk map, using a statistical model based on data from a group of subjects, and a stochastic variable, wherein the statistical model also comprises a second value ($z_i$), being based on the stochastic variable, such as the second value modelling non-measured values. The invention may be seen as advantageous since it acknowledges subject variability in probability of tissue infarction on a voxel-by-voxel basis by taking non-measured values into account, which in turn may enable providing more reliable estimates of probability of infarction.

20 Claims, 11 Drawing Sheets

(51) Int. Cl.
*G01C 11/04* (2006.01)
*G06F 17/18* (2006.01)
*G06F 19/00* (2011.01)

(52) U.S. Cl.
CPC ...... *G06F 19/3431* (2013.01); *G06T 2200/04* (2013.01); *G06T 2207/10088* (2013.01); *G06T 2207/20076* (2013.01); *G06T 2207/30016* (2013.01)

(58) Field of Classification Search
USPC ............ 382/128–134; 378/4, 8, 21–27, 901; 600/407, 410, 425, 427, 183
See application file for complete search history.

(56) References Cited

OTHER PUBLICATIONS

Mouridsen, K. et al., "Predictive Models in Multimodal Imaging" Neurodegeneration in Multiple Sclerosis, Topics in Neuroscience, 2007, pp. 127-149, Part 3.
Wu, Ona et al., "Predicting Tissue Outcome in Acute Human Cerebral Ischemia Using Combined Diffusion- and Perfusion-Weighted MR Imaging" Stroke, 2001, pp. 933-942, vol. 32.
International Search Report for PCT/DK2013/050301 dated Dec. 13, 2013.

* cited by examiner

RISK PREDICTION OF TISSUE INFARCTION

CROSS REFERENCE TO RELATED APPLICATIONS

This application is a U.S. National Phase Application of PCT International Application Number PCT/DK2013/050301, filed on Sep. 19, 2013, designating the United States of America and published in the English language, which is an International Application of and claims the benefit of priority to Danish Patent Application No. PA 2012 70578. The disclosures of the above-referenced applications are hereby expressly incorporated by reference in their entireties.

FIELD OF THE INVENTION

The present invention relates to a method for predicting tissue infarction and more specifically relates to a method, a system and a computer program product for generating a risk map indicating predicted voxel-by-voxel probability of tissue infarction for a set of voxels

BACKGROUND OF THE INVENTION

In acute stroke, one or more major brain arteries are suddenly occluded, resulting in immediate risk of tissue damage downstream from the site of occlusion. Before the patient arrives at hospital, a volume of tissue will typically already have sustained severe injury with little probability of recovering, while surrounding tissue may be functionally impaired but more likely to regain function if blood flow can be reestablished. Therapeutic strategy is dependent on the volume of this tissue, which is likely to recover.

The relation between acute tissue state and extend of the final infarct is highly complex, and therefore, e.g., Magnetic Resonance Imaging (MRI) is used to gain information on a wide range of tissue characteristics. In the acute setting, an experienced radiologist must investigate a correspondingly large body of image types, in multiple regions of the brain, and based on experience infer the likely tissue response to treatment.

WO 01/56466 A2 describes a method of evaluating novel stroke treatments which includes generating a risk map indicative of the probability of tissue infarction on voxel-by-voxel basis and selecting a probability range for evaluating the therapeutic effect of the novel treatment. In one particular embodiment, tissue having a fifty percent probability of tissue infarction is selected. A novel treatment that has a reduced level of overall actual infarction as compared to the predicted value is indicative of therapeutic effect.

An improved method to generate a risk map indicative of the probability of tissue infarction on a voxel-by-voxel basis would be advantageous, and in particular a more efficient, reliable, fast, reproducible and/or automated method to generate a risk map indicative of tissue infarction on a voxel-by-voxel basis would be advantageous.

SUMMARY OF THE INVENTION

It is a further object of the present invention to provide an alternative to the prior art.

In particular, it may be seen as an object of the present invention to provide a method, a system and a computer program product for generating a risk map indicating predicted voxel-by-voxel probability of tissue infarction for a set of voxels that solves the above mentioned problems of the prior art with efficiency, reliability, time consumption, reproducibility and/or need for manual input, such as input from an experienced radiologist and which acknowledges and quantifies subject variability in probability of tissue infarction on a voxel-by-voxel basis.

Thus, the above described object and several other objects are intended to be obtained in a first aspect of the invention by providing a method for generating a risk map indicating predicted voxel-by-voxel probability of tissue infarction for a set of voxels, the method comprising, such as comprising the steps of, receiving for each voxel a first value (x), where each first value (x) corresponds to a set of tissue marker values being representative of a quantity, such as a measurable quantity, which is representative of the corresponding voxel, and generating the risk map, wherein the risk map is generated using a statistical model based on data, such as data from a plurality of imaging techniques, from a group of subjects, and a stochastic variable, and wherein the statistical model receives as input for each voxel the first value (x), and wherein the statistical model further receives as input
a second value ($z_i$), being based on the stochastic variable, such as the second value modelling non-measured values, and which statistical model outputs the risk map.

The invention is particularly, but not exclusively, advantageous for obtaining a method for generating a risk map indicating predicted voxel-by-voxel probability of tissue infarction for a set of voxels efficiently, reliably, fast, reproducibly and/or automatically, since the method takes as input tissue marker values and outputs the risk map. The method may be seen as efficient since it requires no judgements from trained personnel, and the method may further be seen as reliable since the lack of manual input minimizes the influence of human errors. Also, the lack of judgements may make the method reproducible. Furthermore, the invention may be seen as advantageous since it acknowledges subject variability in probability of tissue infarction on a voxel-by-voxel basis by taking non-measured values into account, which in turn may enable providing more reliable estimates of probability of infarction.

The basic insight underlying the invention may be seen as the insight that non-observed factors do play a role for the individual subjects, which offsets tissue probability of infarct. While this may not be observed on the subject level, it may be observed on the level of a population, such as within the group of subjects upon which the statistical model is based, such as within the group of subjects which comprises a plurality of subjects upon which the statistical model is based. This knowledge may then in turn be utilized in methods according to the invention, which takes this effect into account by implementing one or more stochastic variables in the statistical model.

By an image is understood a set of data points representative of a spatially resolved parameter, such as a set of spatially resolved values, where each data point corresponds to a value of a parameter in a position. It is understood that the positions may be comprised within a plane, corresponding to a two-dimensional image, or they may be distributed across more dimensions, for example three dimensions. It is further understood that each data-point may correspond to a finite area or volume, such as having a finite area or finite volume being assigned to each data point, although the position is described as a mathematically ideal point in space. In the present application 'map' is used interchangeably with 'image'.

By 'risk map' is understood a map with data points representative of a spatially resolved parameter, where the parameter is a predicted voxel-by-voxel probability of tissue infarction.

By 'infarction' is understood an area of irreversibly damaged tissue which has permanently lost its function.

By 'a first value' is understood a set of tissue marker values, such as a multi-dimensional vector, being representative of a quantity, such as a measurable quantity, which is representative of the corresponding voxel. For example, a first value for a voxel may be a set of tissue marker values for Diffusion Weighted Imaging (DWI) and Perfusion Weighted Imaging (PWI), i.e., the DWI value for the particular voxel and the PWI value for the particular voxel. It may be understood that the set of tissue marker values corresponds to a plurality of tissue marker values, where each tissue marker value is representative of a quantity, such as a measurable quantity, which is representative of the corresponding voxel. For example, the first value may in exemplary embodiments correspond to a vector representative of a DWI value and a PWI value, where the first value for each voxel may thus comprise a DWI value corresponding to the DWI value of the voxel (such as measured in the voxel) and a PWI value corresponding to the PWI value of the voxel (such as measured in the voxel). It is further understood, that an image or map, such as for example a DWI image or a PWI image, may correspond to a single tissue marker value (in the first value) which is spatially resolved corresponding to the positions of a plurality of voxels.

'Statistical model' is understood as is general in the art, as a formalization of relationships between variables in the form of mathematical equations, which describes how one or more random variables, such as the tissue marker values in the first value are related to one or more random variables, such as the observed voxel-by-voxel tissue outcome (such as "infarction" or "survival"). The statistical model is understood to be based on data, such as data corresponding to the tissue marker values in the first value, such as data from a plurality of imaging techniques (such as DWI and PWI), from a group of subjects, such as data including voxel-by-voxel outcome (e.g., "infarction" or "survival") after a period of time, such as corresponding voxel-by-voxel outcome. It may be understood that the group of subjects comprises a plurality of subjects, such as a plurality of patients, such as a plurality of human patients. It may be understood that the number of voxels associated with each subject may be larger than 1, such as significantly larger than 1, such as at least 32, 64, 128, 256, 512, 1024, 2048, 4096, 8192 or 16384. It may in general be understood that 'group of subjects' may be used interchangeably with 'plurality of subjects'.

The second value ($z_i$) is based on the stochastic variable, such as the second value modelling non-measured values.

'Stochastic variable' is commonly known to the skilled person, and is understood to denote a numerical quantity defined in terms of the outcome of a random experiment. Mathematically, it is a function defined on a probability space taking on either integer values or real values.

It may be understood the stochastic variable may represent non-measured values in the group of subjects. The making of the statistical model may comprise quantifying the stochastic properties of the stochastic variable z, which in turn may enable providing the second value $z_i$, which may in turn be chosen in exemplary embodiments to reflect any one of patient average outcome, mean value of the stochastic variable, upper bound (such as, a value which some fraction of the sample lies below), lower bound (such as, a value which some fraction of the sample lies below). In a specific embodiment, a plurality of risk maps is generated, wherein each risk map in the plurality of risk maps correspond to different second values $z_i$.

In the present context, it is understood that the second value $z_i$ may model non-measured values. For an individual subject, the non-measured value (the "individual" second value $z_i$) may be understood to have a fixed value. However, for different subjects, the non-measured values may take on different values. For a plurality of subjects, the second value may model these non-measured values. In other words, the individual subject is associated with a specific non-measured value, but this specific value is not known and can for this reason not be put into the model. However, by having observed a plurality of subjects, it may be estimated what the non-measured values could be, and this enables that these non-measured values may be put into the statistical model.

Voxel is commonly known in the art and is understood to be an entity representing a given volume, such as a volume within a biological tissue. A voxel may be assigned a value of a parameter, such as a perfusion parameter or a diffusion parameter. One or more voxels may constitute an image.

By 'voxel-by-voxel probability of tissue infarction' is understood the probability of tissue infarction for each individual voxel.

The tissue marker values may be related to any metric. In the present application, imaging modalities and metric is used interchangeably. A non-limiting set of metrics may comprise: TTP, MTT, ADC, DWI, CBF, and CBV.

Time-to-peak (TTP) images are commonly known in the art and a TTP image is understood to be an image where the spatially resolved parameter corresponds to a length of a time interval from a start time to a time corresponding to a maximum of a tissue concentration curve measured in a given position.

Apparent Diffusion Coefficient (ADC) images are commonly known in the art and an ADC image is understood to be an image where the spatially resolved parameter corresponds to a measure which quantifies, represents or relates to the mobility of molecules in their microenvironment, in particular the dynamic displacements of water molecules. The ADC image intensities are in absolute scale.

Cerebral Blood Flow (CBF) is commonly known in the art and refers to the rate of delivery of blood to tissue. In DSC MRI, CBF is typically calculated for each volume element (voxel) by the maximum function value of the deconvolved tissue curve.

Cerebral blood volume (CBV) is commonly known in the art and refers to the volume fraction of blood in a tissue region. In DSC MRI, CBV is often calculated as the area under the contrast agent concentration curve, and normalized by the area under the arterial input function.

Mean-transit-time (MU) images are commonly known in the art and a MTT image is understood to be an image where the spatially resolved parameter corresponds to the mean lead time of a fluid, such as blood, through the capillaries of biological tissue. The MTT value may in an exemplary embodiment be determined by the ratio CBV/CBF.

In an embodiment, there is provided a method wherein the first value includes Diffusion Weighted Imaging (DWI) data and/or Perfusion Weighted Imaging (PWI) data.

A possible advantage of using PWI and DWI data may be that these metrics have been shown valuable in terms of predicting infarction.

By diffusion parameter is understood a measure which quantifies, represents or relates to the mobility of molecules in their microenvironment, such as the dynamic displacements of water molecules.

Diffusion Weighted Imaging (DWI) is commonly known in the art and refers to measurement of mobility of molecules in their microenvironment. Diffusion Weighted Imaging (DWI) data are understood to be the values of the voxels in a DWI image.

By perfusion parameter is understood a measure which quantifies, represents or relates to the passage of fluid through an element, such as a biological tissue, such as a biological organ, in particular the delivery of arterial blood to the capillaries.

Perfusion weighted imaging (PWI) is commonly known in the art. Perfusion Weighted Imaging (PWI) data are understood to be the values of the voxels in a PWI image. A PWI image may be based on any of the non-limiting set of metrics including MTT, TTP, CBF, CBV.

By 'set of voxels' may in embodiments be understood that the set of voxels may be belonging to a single subject, such as a single patient, such as a single human patient. It may in embodiments be understood that the set of voxels comprises voxels in a brain. It may in a specific embodiment be understood that the set of voxels consists of voxels in a brain.

In another embodiment, there is provided a method wherein the method further comprises the step of
generating a plurality of risk maps, where each risk map in the plurality of risk maps, corresponds to a particular value of the second value.

A possible advantage of such plurality of risk maps may be that depending on the value of the second value, the risk map may—for example—be taken as representative of upper or lower risk bounds. Thus, in addition to obtaining a prediction of future values, it may also be possible to obtain information regarding the variability of this prediction given the un-measured variation in outcome, i.e., how subject heterogeneity may offset the predicted value. This may be seen as being made possible since the making of the statistical model comprises quantifying the stochastic properties of the stochastic variable z, which in turn enables providing the second value $z_i$, which may in turn be chosen in exemplary embodiments to reflect patient average outcome, or mean value of the stochastic variable, an upper bound or a lower bound.

Regarding the statistical model, it is understood, that the coefficients corresponding to each element of x (i.e., each tissue marker) as well as a quantification of the stochastic properties of the stochastic variable z, may be generated based on data, such as data from a plurality of imaging techniques and/or imaging modalities, such as data from a group of subjects. For example, a method for generating the coefficients corresponding to each element of x (i.e., each tissue marker) as well as a quantification of the stochastic properties of the stochastic variable z may comprise
receiving for a plurality of voxels for each voxel a first value (x), where each first value (x) corresponds to a set of tissue marker values being representative of a quantity, such as a measurable quantity, which is representative of the corresponding voxel,
and which outputs coefficients corresponding to each element of x as well as a quantification of the stochastic properties of the stochastic variable z. With these quantities, a risk map can be produced for a patient given when voxel values x are given as input.

The method for generating the coefficients corresponding to each element of x (i.e., each tissue marker) as well as a quantification of the stochastic properties of the stochastic variable z may optionally also comprise any one of
receiving patient related information, such as clinical findings or treatment decision,
receiving data related to follow-up studies indicative of the extent of final infarct volume for a given subject.

It may be understood that patient related information may be part of the information in the first value.

In another embodiment, there is provided a method wherein the data from the group of subjects comprises an actual tissue infarction state, such as an actual tissue infarction state for a subject being represented by the first value, such as an actual follow-up tissue infarction state for a subject being represented by the first value. It may be understood that the data from the group of subjects comprises (such as comprises for each voxel in a group of one or more voxels in each subject) both
a first value, such as a set of tissue marker values being representative of a quantity, such as a measurable quantity, which is representative of the voxel or voxels in each subject in the group of subjects. It may be understood that 'the first value' for a voxel in a subject may not be identical to 'the first value' (x) which represents the voxel for which a prediction of tissue infarction is desired, but it may describe numerical values of the similar tissue marker values.
an actual follow-up tissue infarction state.

In another embodiment, there is provided a method further comprising
receiving a background map based on follow-up images for a secondary group of subjects, such as primarily based on follow-up images for a secondary group of subjects, such as substantially based on follow-up images for a secondary group of subjects, such as substantially exclusively based on follow-up images for a secondary group of subjects, such as exclusively based on follow-up images for a secondary group of subjects, said background map being indicative of infarct likelihood as a function of spatial position,
and wherein the risk map is generated using also the background map.

It is understood that the 'secondary group of subjects' may be smaller than—, equal to—larger than the group of subjects (upon which the statistical model of the previous embodiments is based and which in an alternative formulation may be referred to as 'primary group of subjects'), it may be overlapping or not overlapping with the group of subjects. In a specific embodiment, the 'secondary group of subjects' in the present embodiment is numerically larger than the group of subjects.

It may be seen as a key insight underlying the present embodiment that when follow-up images are used in conjunction with acute images, predictions may potentially be obscured by artifacts in the acute images. In other words, if the data from the group of subjects (upon which the statistical model is based) comprises outliers or noisy data resulting in non-physiological values of tissue marker values corresponding to the first value, then the deterministic parameters in the model may be somewhat incorrect. Furthermore, if the data from the subject (for which the risk map is generated) comprises outliers or merely data resulting in non-physiological values of tissue marker values corresponding to the first value, then the prediction for the corresponding voxels may be somewhat incorrect. However, by incorporating the background map into the method as suggested in the present embodiment, the critical follow-up information may be employed independently of the noise which is inherent in acute modalities (i.e., acute modalities potentially corresponding to one or more tissue marker values in the first value). The present embodiment thus effectively strengthens overall performance, such as by decreasing estimated risk due to noise in areas remote from areas prone to tissue infarction and by increasing confidence within the areas prone to tissue infarction.

An advantage of this embodiment may thus be that it enables that the follow-up images, such as the follow-up images alone, can be used to
  (a) increase the spatial accuracy of the method for generating the risk map, and/or
  (b) increase the overall performance of the method by allowing a considerably larger amount of available data from clinical studies to be incorporated. It is noted that in general, larger amounts of It is furthermore noted that potential advantages thus include that one or more of the potential problems that
  (1) the scan images, such as the tissue marker values corresponding to the first value, may exhibit considerable noise. Especially perfusion-based metrics, such as PWI images, where noise is compounded by so-called deconvolution techniques, which by a spatially uninformed model typically translates into random high-risk predictions scattered throughout the risk map, and/or
  (2) relatively few datasets are available to be fed into the statistical model, since only datasets where complete scans upon admission as well as at follow-up are acquired (such as datasets comprising data corresponding to all the tissue marker values corresponding to the first value in the model) can be used to establish the statistical model, leaving out in practice the majority of clinical data acquired until now where, e.g., MRI was not performed upon admission because of timing, logistics or availability only of techniques incapable of providing sufficient data, such as (in certain circumstances) CT imaging.

may be partially or fully alleviated by employing the present embodiment.

In a further embodiment, the step of providing the background map comprises
  identifying voxels representative of tissue infarction, such as permanent lesions, on each of the follow-up images for the secondary group of subjects,
  providing the background map based on information regarding spatial positions of the voxels representative of tissue infarction on each of the follow-up images for the secondary group of subjects.

In a further embodiment, the step of providing the background map further comprises transformations of said background map, such as transformations in order to attenuate low risk and/or strengthen high risks.

In another further embodiment, there is provided a method wherein the risk map is based on the background map by having the statistical model being based on said data (104) from a group of subjects and said stochastic variable and the background map. For example, the background map may be merged with the method according to any previous embodiment by entering it as an additional value in the first set of values along with the tissue marker values.

In another further embodiment, there is provided a method wherein the risk map is based on the background map by having the statistical model based on said data (104) from a group of subjects and the stochastic variable output the risk map, and wherein said risk map is subsequently modified based on the background map. For example, the risk map may be generated based on the statistical model (which may not be based on the background map), and the risk may subsequently be amended based on the background map, such as the risk map thus amended being a weighted average of the risk map output from the statistical model and the background map.

In another embodiment, there is provided a method wherein the statistical model is given by $$Pr(\text{Infarct}|x) = G(\alpha, z, x),$$

where $Pr(\text{Infarct}|x)$ is the risk of infarct for a voxel, the first value $x = (x_1, x_2, \ldots, x_K)$ corresponds to each of K tissue marker values for the voxel, $\alpha$ is a set of weights assigned to each of K tissue marker values, z is the stochastic variable, upon which the second value $z_i$ is based, and G is a non-linear mathematical function. By estimating subject specific tendency of tissue to infarct (where subject specific tendency of tissue to infarct is modelled with the stochastic variable, upon which the second value $z_i$ is based) as described in this embodiment, a bias in model coefficients is resolved, such that shrinkage towards zero as patient heterogeneity increases is avoided. The model parameters may thus be seen as unbiased since the stochastic variable accounts for variations in infarct likelihood across patients. A possible advantage of this embodiment may thus be that it enables a method which provides unbiased estimates of the effect of tissue markers and treatment efficacy and acknowledges and quantifies subject variability in probability of tissue infarction on a voxel-by-voxel basis. It is mentioned, that if the stochastic variable were not included in the model, increasing the number of subjects used to generate the model would be likely to also increase the heterogeneity which in turn would lead to less difference in probability to infarct for different input values. This could be seen as unfortunate, in particular as the model would become less useful for predicting outcome of treatments and thus less useful as a decision support system.

In another embodiment, there is provided a method wherein the statistical model is given by $$Pr(\text{Infarct}|x) = G\left(\sum_{j=1}^{K} \alpha_j(z) x_j\right),$$

where $Pr(\text{Infarct}|x)$ is the risk of infarct for a voxel, the first value $x = (x_1, x_2, \ldots, x_K)$ corresponds to each of K tissue marker values for the voxel, $\alpha(z) = (\alpha_1(z), \alpha_2(z), \ldots, \alpha_K(z))$ are weights assigned to each of K tissue marker values, z is the stochastic variable upon which the second value $z_i$ is based, and G is a mathematical function.

The weights assigned to each of K tissue marker values are estimated during model fitting, i.e., generated when creating the statistical model.

The mathematical function G may in general be any function which takes values in the interval [0,1].

The stochastic variable z may in general have either a discrete or continuous distribution.

In a further embodiment, there is provided a method wherein the mathematical function G may be chosen from the set comprising:
  a logistic-like function, such as a logistic function, such as a function mathematically described by $$G(t) = \frac{1}{1 + \exp(-t)}$$

a probit-like function, such as a probit function, such as a function mathematically described by $$G(t) = \frac{1}{\sqrt{2\pi}} \int_{-\infty}^{t} \exp(-h^2/2)\,dh$$

a function substantially similar to a complementary log-log regression, such as a complementary log-log regression, such as a function mathematically described by $G(t)=1-\exp(-\exp(t))$.

By the suffix '-like' is emphasized that minor deviations from, e.g. a logistic function, may still be within the scope of the claimed embodiment. In some specific embodiments, the mathematical function G may be chosen, such as is chosen, from the set comprising: an exact logistic function, an exact probit function, an exact complementary log-log regression.

In another further embodiment, there is provided a method wherein the stochastic variable z is given by a probability density function, such as a Gaussian density.

In another embodiment, there is provided a method wherein the statistical model is given by $$\Pr(Infarct\,|\,x) = \frac{1}{1 + \exp(-z - \alpha_1 x_1 - \ldots - \alpha_K x_K)},$$

where $\Pr(Infarct|x)$ is the risk of infarct for a voxel, the first value $x=(x_1, x_2, \ldots, x_K)$ corresponds to each of K tissue marker values for the voxel, $\alpha=(\alpha_1, \alpha_2, \ldots, \alpha_K)$ are weights assigned to each of K tissue marker values, z is the stochastic variable, upon which the second value $z_i$ is based. In this embodiment, only the intercept varies, and the function G is given by the logistic function. It may be understood that minor deviations from the equation may still be within the scope of the claimed embodiment.

In another embodiment there is provided a method wherein the stochastic variable z is given by $$p(z)=N(0,\sigma^2),$$

where $N(0,\sigma^2)$ is a Gaussian-like distribution, such as a Gaussian distribution with zero mean and non-zero standard deviation $\alpha$. In this embodiment, the stochastic variable z is given by a probability density function which is a Gaussian density with zero mean and non-zero standard deviation.

In another embodiment, there is provided a method wherein the statistical model is given by $$\Pr(Infarct\,|\,x) = \sum_{m=1}^{M} \Pr(z = z_m) \frac{1}{1 + \exp\left(-z_m - \sum_{j=1}^{K} \alpha_j x_{ji}\right)},$$

where $\Pr(Infarct|x)$ is the risk of infarct for a voxel, the first value $x=(x_1, x_2, \ldots, x_K)$ corresponds to each of K tissue marker values for the voxel, $\alpha=(\alpha_1, \alpha_2, \ldots, \alpha_K)$ are weights assigned to each of K tissue marker values, and the stochastic variable z is given by the set $(z_1, \ldots, z_M)$ of M discrete, possible values. In this embodiment, the stochastic variable z may assume a discrete set of values. It may be understood that minor deviations from the equation may still be within the scope of the claimed embodiment.

In another embodiment, there is provided a method wherein the method further comprises the step of
generating a plurality of risk maps, such as a plurality of risk maps corresponding to a plurality of groups of subjects, each of which is generated using said statistical model based on data from a group of subjects, such as a group of subjects within the plurality of groups of subjects, each group of subjects, such as each group of subjects within the plurality of groups of subjects, having been treated with a particular therapy.

A possible advantage of generating such plurality of risk maps may be that since the determined risk of infarction is based on different therapies, it may enable selection of a therapy which has a relatively low risk of infarction, such as by comparison with the risk of infarction of other therapies. It is further noted, that since risk intervals may also be obtained with the method, it may also enable selecting a therapy which has a high certainty of a certain risk.

By 'each of which is generated using said statistical model based on data from a group of subjects' may in general be understood that different statistical models are employed for each generation of a risk map (within the 'generating a plurality of risk maps'). It may further be understood that the difference between the different statistical models may be due to differences in the groups of subjects from which the data for the different statistical models originate. In other words, different groups of subjects (such as different groups of subjects having each been treated with a particular therapy), may entail different data, which in turn may entail different statistical models, which in turn may entail different risk maps (which correspond to the 'plurality of risk maps').

Within the context of the present application, 'therapy' is used interchangeably with 'treatment'.

In another embodiment, there is provided a method wherein the method further comprises the step of determining a volume of tissue which is likely to be infarcted.

An advantage of determining a volume which is likely to be infarcted may be, that it provides a simple value, i.e., 'volume', which may relatively easily be compared across, e.g., therapies, subjects, time, etc.

In another embodiment, there is provided a method wherein the method further comprises the steps of
generating a plurality of risk maps, such as a plurality of risk maps corresponding to a plurality of groups of subjects, each of which is generated using said statistical model based on data from a plurality of subjects, such as a group of subjects, such as a group of subjects within the plurality of groups of subjects, each plurality of subjects, such as each group of subjects, such as each group of subjects within the plurality of groups of subjects, having been treated with a particular therapy, and
for each of said risk maps, determining a volume of tissue which is likely to be infarcted.

This embodiment may enable predicting, such as predicting and comparing, risk maps via the statistical model, where the statistical model used to generate each risk map may differ with respect to the statistical model used to generate other risk maps, due to differences in the data between the different sets of 'plurality of subjects' which is used for generating the coefficients in the statistical model. A possible advantage of this may be that volumes which are likely to be infarcted may be obtained for a plurality of therapies, which in turn provides a simple way of comparing therapies.

In a further embodiment there is provided a method wherein the volume of tissue which is likely to be infarcted is determined by calculating the sum, over all voxels, of the product between the volume of each voxel multiplied by the probability of infarct for said voxel. The volume may in an exemplary embodiment be calculated according to the formula: $\Sigma_j(\text{volume}_j*\text{Pr}(\text{infarct}|x_j))$, where j is summed over all voxels, $\text{volume}_j$ is the volume of the j'th voxel and $\text{Pr}(\text{infarct}|x_j)$ is the risk of infarction of the j'th voxel. A possible advantage of this may be that it yields a realistic estimate of the volume which is likely to be infarcted, since the volumes are weighted with their risk value.

In another embodiment, there is provided a method wherein the method further comprises the step of receiving patient related information, such as clinical findings.

The patient related information may comprise patient related information, such as gender or age, or clinical findings, such as the presence of a disorder, disease, or underlying condition, such as diabetes. In particular embodiments, the patient related information may include treatment. A possible advantage of including treatment in the patient related information may be that it enables forming a risk map corresponding to the particular treatment, which may in turn enable predicting the effect of a type of treatment.

According to a second aspect the invention relates to a system comprising a processor arranged for carrying out the method according to the first aspect.

In a further embodiment there is provided a system, wherein the system furthermore comprises an apparatus arranged for obtaining one or more first values, such as a nuclear magnetic resonance (NMR) scanner.

In a third aspect the invention relates to a computer program product enabled to carry out the method according to the first aspect, such as a computer program product being adapted to enable a computer system, such as the computer system according to the second aspect, comprising at least one computer having data storage means in connection therewith to control an apparatus, such as an NMR scanner. This aspect of the invention is particularly, but not exclusively, advantageous in that the present invention may be accomplished by a computer program product enabling a computer system to carry out the operations of the system of the second aspect of the invention when down- or uploaded into the system. Such a computer program product may be provided on any kind of computer readable medium, or through a network.

The first, second and third aspect of the present invention may each be combined with any of the other aspects. These and other aspects of the invention will be apparent from and elucidated with reference to the embodiments described hereinafter.

BRIEF DESCRIPTION OF THE FIGURES

The method, system and computer program product according to the invention will now be described in more detail with regard to the accompanying figures. The figures show one way of implementing the present invention and is not to be construed as being limiting to other possible embodiments falling within the scope of the attached claim set.

DETAILED DESCRIPTION OF AN EMBODIMENT

Figure 1:
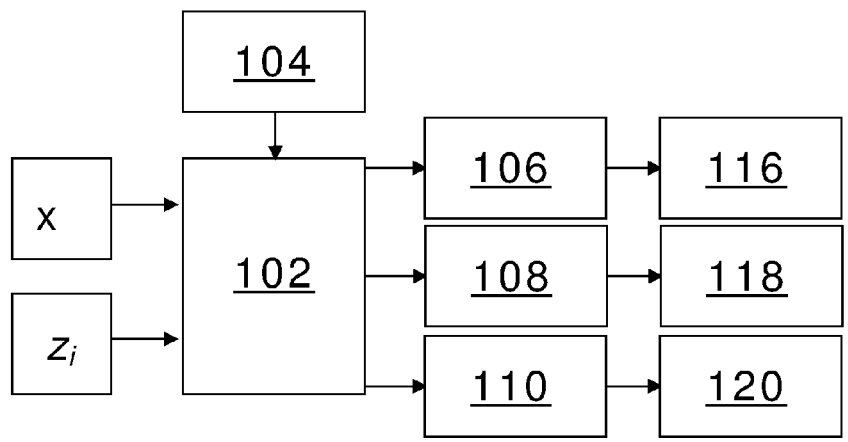
FIG. 1 shows a schematic illustration of a method according to an embodiment of the invention.

FIG. 1 shows a schematic illustration of a method according to an embodiment of the invention, wherein a first value x and a second value $z_i$, being based on a stochastic variable, are put into a statistical model 102, which statistical model is based on data 104, such as data from a plurality of imaging techniques, from a group of subjects and the stochastic variable. The statistical model in turn outputs a risk map 106 indicating predicted voxel-by-voxel probability of tissue infarction for a set of voxels. In the embodiment shown, the statistical model 102 outputs risk maps 108, 110, where the risk maps 106, 108, 110 corresponds to a plurality of risk maps, where each risk map in the plurality of risk maps, corresponds to a particular value of the second value. Furthermore, the method comprises determining a volume 116 of tissue which is likely to be infarcted (for a particular value of the second value corresponding to risk map 106), wherein the volume of tissue which is likely to be infarcted is determined by calculating the sum, over all voxels, of the product between the volume of each voxel multiplied by the probability of infarct for said voxel. Similar volumes 118, 120 are calculated for the risk maps 108, 110 for the other values of the second value. In other embodiments, a plurality of risk maps 106, 108, 110 and corresponding volumes 116, 118, 120 of tissue which is likely to be infarcted, may be generated using statistical models based on data for different pluralities of subjects, such as each plurality of subjects having been treated with different therapies.

Figure 2:
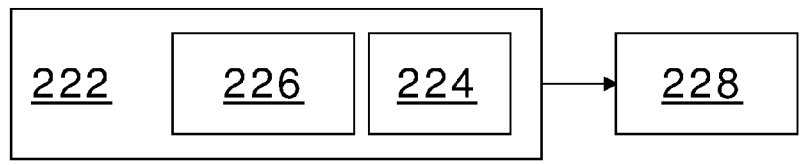
FIG. 2 shows a system according to an embodiment of the invention.

FIG. 2 shows a system 222 according to an embodiment of the invention, the system comprising a processor 224 arranged for carrying out the method according to the first aspect, and the system furthermore comprises an apparatus 226 arranged for obtaining one or more first values, the apparatus being a nuclear magnetic resonance scanner in the present embodiment. The system is arranged for outputting the risk map to a receiving unit 228, which may, in exemplary embodiments, be any one of a computer screen, a network connection, or a computer readable storage device.

Figure 3:
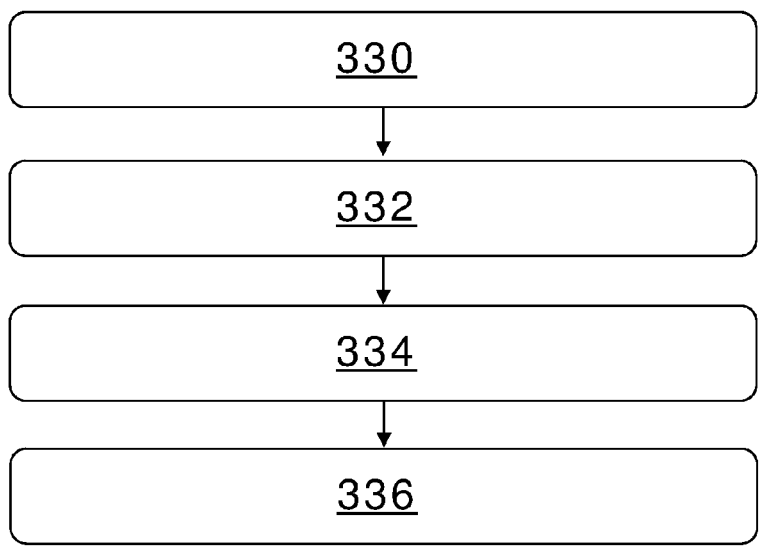
FIG. 3 is a flow-chart of a method for generating a risk map indicating predicted voxel-by-voxel probability of tissue infarction for a set of voxels.

FIG. 3 is a flow-chart of a method for generating a risk map indicating predicted voxel-by-voxel probability of tissue infarction for a set of voxels, the method comprising the steps of receiving 330 for each voxel a first value (x), where each first value (x) corresponds to a set of tissue marker values being representative of a quantity, such as a measurable quantity, which is representative of the corresponding voxel, and generating 332 the risk map, wherein the risk map is generated using a statistical model based on data, such as data from a plurality of imaging techniques, from a group of subjects, and a stochastic variable, and wherein the statistical model receives as input for each voxel the first value, and wherein the statistical model further receives as input a second value ($z_i$), being based on the stochastic variable, such as the second value modelling non-measured values, and which outputs 334 the risk map.

The exemplary method furthermore comprises the step of determining 336 a volume of tissue which is likely to be infarcted.

It is proposed to estimate the expected risk of tissue infarction at the level of image tissue volumes (voxels). It is further proposed to estimate the difference in expected risk of tissue infarction at the level of image tissue volumes (voxels) given 2, 3, 4, 5, 6, 7, 8, 9, 10 or more treatment options. This prediction is made based on the actual tissue progression history in all available previous subjects, such as patients, by associating any number of imaging modalities, such as any number of imaging modalities acquired at admission to hospital, with final tissue outcome. It is anticipated that patients differ in tolerance to ischemia, and that these differences prevent meaningful predictions of outcome based on a single mechanistic association between acute findings and final outcome.

Formally, the coefficients in a model relating acute values, such as the pluralities of first values for all voxels, to final outcome should depend on a particular subjects' inherent, but unobserved, tolerance to ischemia $$\Pr(Infarct \mid x, z_i) = G\left(\sum_{j=1}^{K} \alpha_j(z_i) x_{ji}\right) \quad [1]$$

where the first value x corresponds to a set of tissue marker values ($x_1, x_2, \ldots, x_K$) so that $x=(x_1, x_2, \ldots, x_K)$ contains the values of the tissue markers in a given voxel, and $\alpha(z_i)=(\alpha_1(z_i), \alpha_2(z_i), \ldots, \alpha_K(z_i))$ are the weights assigned to each tissue marker, and which are estimated during model fitting. It is common to use the logistic function $$G(v)=1/1+\exp(-v)$$

when modelling probabilities, however, the use of other functions is also encompassed by the present invention.

The variable $z_i$ in equation [1] above indicates that the coefficients are different for different subjects (with index i). The value of $z_i$ is not known a priori and is not necessarily directly observed, but, as shown in the present application, it quantitatively affects tissue risk of infarction. In the present application it is demonstrated that contradictory conclusions about treatment effects are reached when subject differences are neglected, proposed that prediction of tissue risk of infarction should be based on anticipated subject specific tolerance to ischemia, and proposed that coefficients may be biased if subject heterogeneity is neglected.

Figure 4:
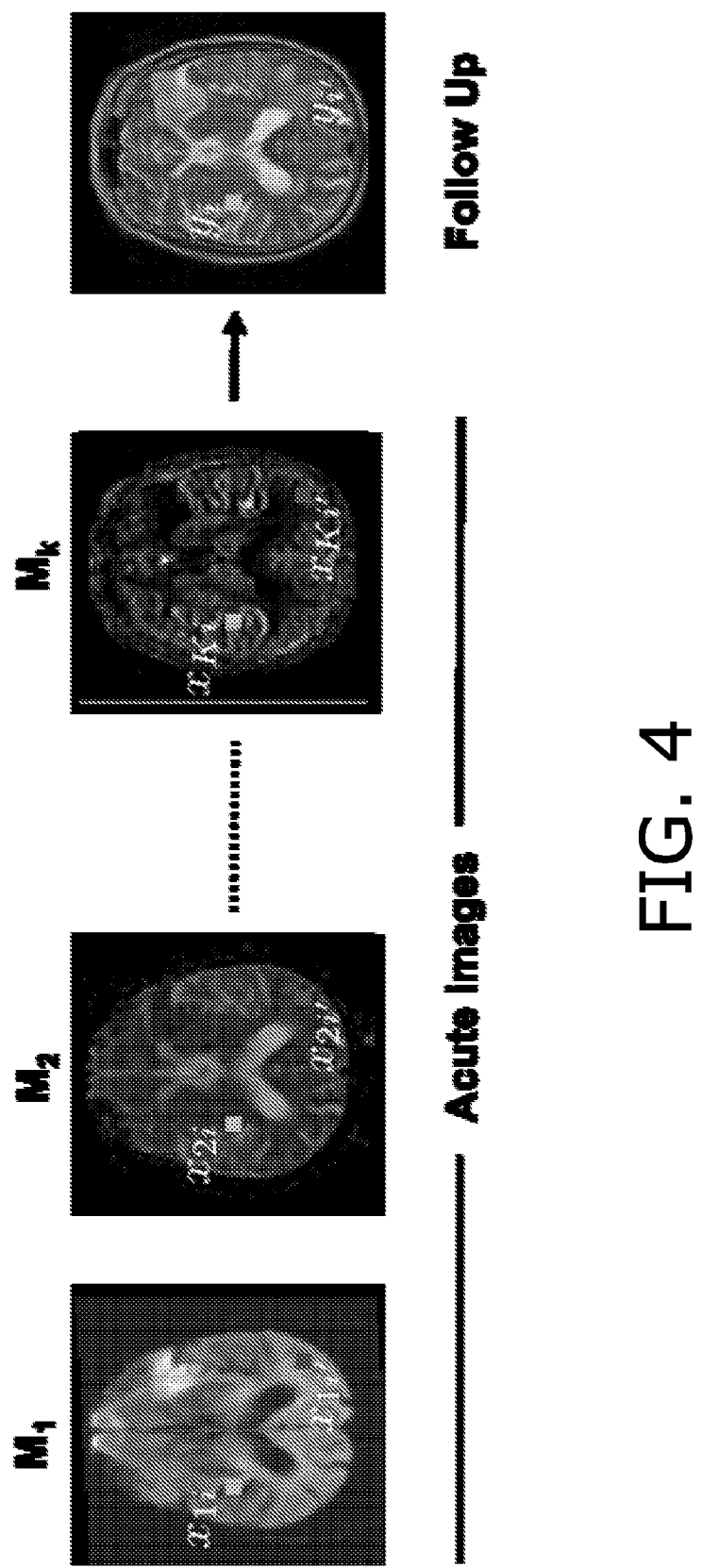
FIG. 4 illustrates the basic principle of relating acute voxel values to follow up voxel values.

FIG. 4 illustrates the basic principle of relating acute voxel values to follow up voxel values, such as final outcome. The images $M_1$-$M_k$ originate from different imaging modalities, such as DWI and PWI, where each image, which is interchangeably referred to as 'map', as is generally understood in the art, corresponds to a spatially resolved set of values of tissue marker values. The voxel values $x_{1i}$-$x_{Ki}$ correspond to the first value for that particular voxel (shown in light grey in the left side of the image). Correspondingly, $x_{1i'}$-$x_{Ki'}$ correspond to the first value for another particular voxel (shown in dark grey in the right side of the image). The voxel shown in dark grey in the right side of the image infarcts (as can be seen in the Follow Up image), while the voxel shown in light grey in the left side of the image survives.

Previous Reference

In the reference WO 01/56466 A2 a standard regression approach is adopted to link a linear (Generalized Linear Model (GLM)) or nonlinear (General Additive Model (GAM)) combination of tissue markers to the risk of tissue infarct.

In the following we consider a data set consisting of N=56 stroke patients with 0 hour, 2 hour and 1 month MRI data. For these patients it could be determined whether the tissue experienced reperfusion, defined here as a reduction of the acute penumbra by at least 20% within 2 hours. Reperfusion has been demonstrated to be associated with a more favorable outcome.

Fitting a standard Generalized Linear Model (GLM) to this data (M=127268 data points from N=56 patients) the following weights are obtained for MTT (perfusion measures), DWI (diffusion measures) and the effect of reperfusion.

|  | Estimate | Std. Error | z value | Pr(>\|z\|) | |
|---|---|---|---|---|---|
| (Intercept) | −3.518895 | 0.025851 | −136.12 | <2e−16 | * * * |
| MTT | 0.104088 | 0.001286 | 80.91 | <2e−16 | * * * |
| DWI | 2.780889 | 0.020957 | 132.69 | <2e−16 | * * * |
| reperf.vox1 | 0.185506 | 0.013071 | 14.19 | <2e−16 | * * * |

It is noted that increasing perfusion and diffusion abnormality increases the risk of local tissue infarction. However, reperfusion is estimated to increase the risk of tissue infarction, thereby exhibiting a harmful effect.

The model assumes reperfusion has the effect of shifting the overall risk of infarct. However, the effect may differ depending on the regional MTT and DWI values.

The model is therefore refitted allowing full interactions between all parameters.

This is formally equivalent to fitting separate models to the two groups

|  | Estimate | Std. Error | z value | Pr(>\|z\|) |  |
|---|---|---|---|---|---|
| (Intercept) | −3.063988 | 0.055785 | −54.925 | <2e−16 | *** |
| MTT | 0.038094 | 0.005732 | 6.646 | 3.02e−11 | *** |
| DWI | 2.287402 | 0.051493 | 44.421 | <2e−16 | *** |
| reperf.vox1 | 0.376472 | 0.073270 | 5.138 | 2.77e−07 | *** |
| MTT:DWI | 0.073878 | 0.005565 | 13.275 | <2e−16 | *** |
| MTT:reperf.vox1 | −0.024016 | 0.008244 | −2.913 | 0.00358 | ** |
| DWI:reperf.vox1 | −0.111086 | 0.068390 | −1.624 | 0.10431 |  |
| MTT:DWI: reperf.vox1 | 0.009482 | 0.007903 | 1.200 | 0.23018 |  |

It is still estimated that reperfusion increases the risk of infarction, although the effect is modified depending on the MTT and DWI values. To examine the net effect the infarct risk is calculated over a range of MTT values at representative DWI values for both groups, see FIGS. 5-6.

Figure 5:
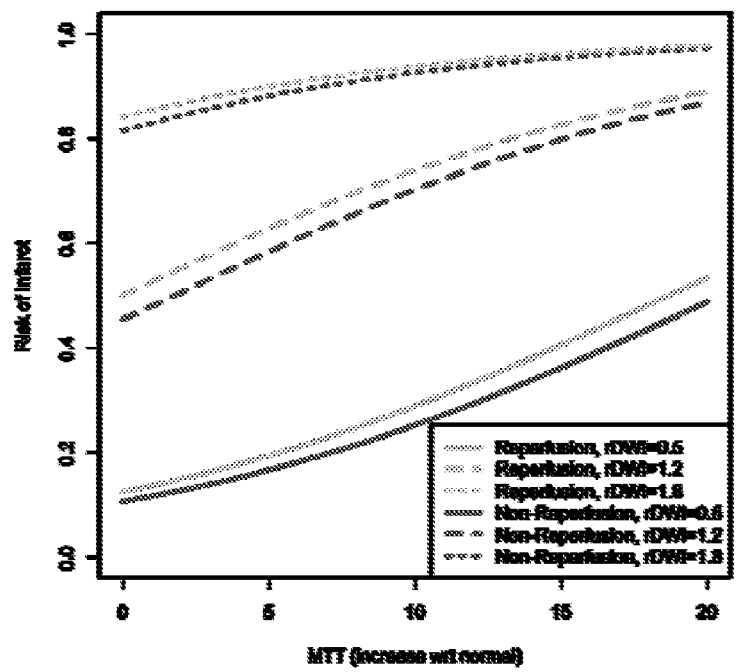
FIG. 5 shows the effect of reperfusion on infarct risk as estimated with the additive model.
Figure 6:
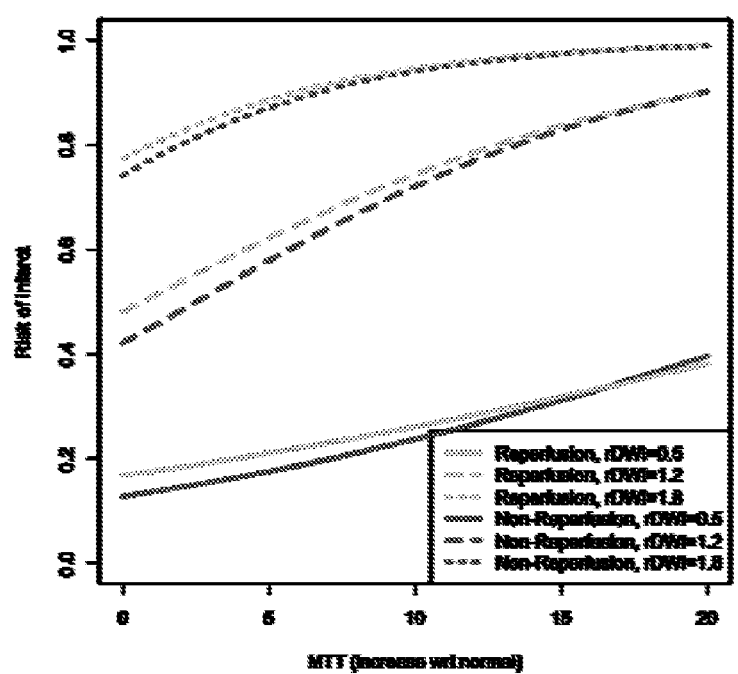
FIG. 6 shows the effect of reperfusion on infarct risk as estimated with separate models for the two groups.

FIGS. 5-6 show the effect of reperfusion on infarct risk. In both figures, the horizontal first axis represents MMT (increase with respect to normal) and the vertical second axis represents Risk of infarct.

FIG. 5 shows the effect of reperfusion on infarct risk as estimated with the additive model, which shows an upward shift in risk with reperfusion.

FIG. 6 shows the effect of reperfusion on infarct risk as estimated with separate models for the two groups, which also shows an upward shift in risk with reperfusion except for extremely high MTT and low DWI.

It is confirmed that even with the separate models reperfusion increases the risk of infarction with the possible exception of extremely high MTT combined with low DWI, where the infarct risk with reperfusion is marginally lower than without reperfusion.

It is possible that the conclusion is a consequence of a poor fit to the underlying data. Therefore the voxel-infarct frequency is calculated for the range of combinations of MTT and DWI and plotted in FIGS. 7-8. The plots in FIGS. 7-8 are model independent and confirm that there is, on average over the patients, a higher risk of infarct with reperfusion in regions with prolonged MTT and normal DWI, i.e., the penumbra.

Figure 7:
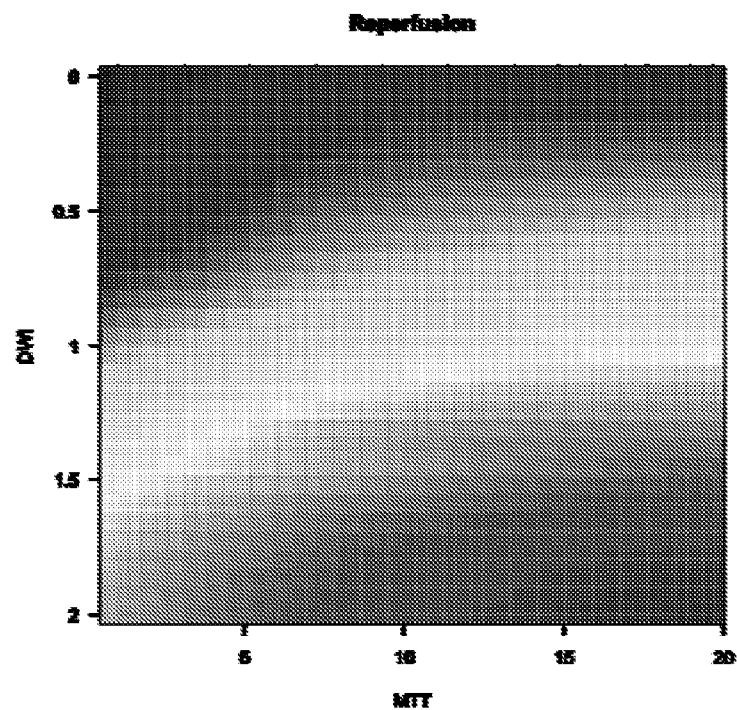
FIG. 7 shows the voxel-infarct frequency in a grey scale plot for voxels with reperfusion.

FIG. 7 shows the voxel-infarct frequency in a grey tone plot for voxels with reperfusion. The highest frequency is given in the lower right corner and the lowest frequency is given in the upper left corner.

Figure 8:
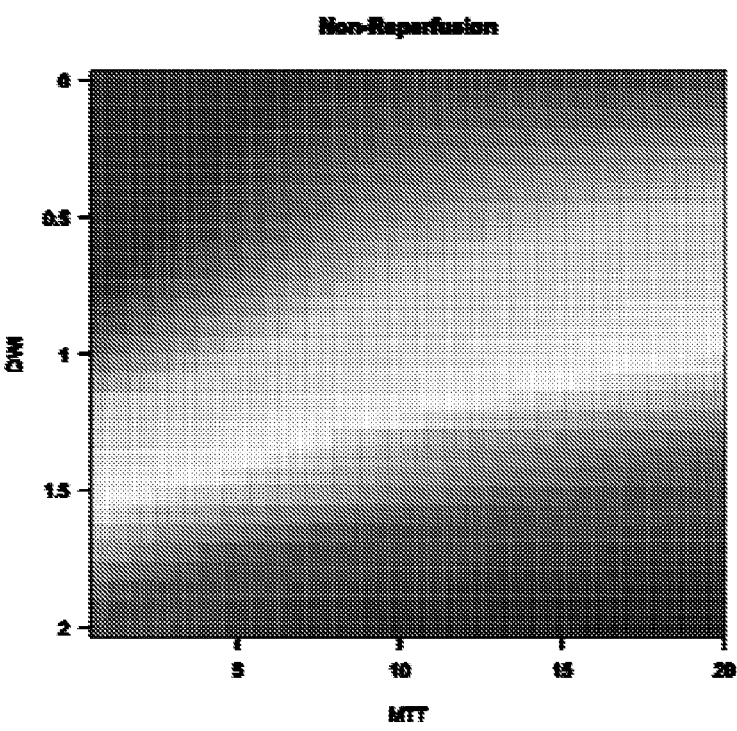
FIG. 8 shows the voxel-infarct frequency in a grey scale plot for voxels without reperfusion.

FIG. 8 shows the voxel-infarct frequency in a grey tone plot for voxels without reperfusion. The highest frequency is given in the lower right corner and the lowest frequency is given in the upper left corner.

Proposed Method

Previous references focus on prediction of the final infarct volume. This is based on a probability score for particular combinations of MRI markers (such as for a first value x) obtained effectively by averaging over a patient cohort. The previous section illustrates that over a wide range of MTT and DWI values probability scores are intermediate between the 'certainties' represented by probabilities 0 (certain survival) and 1 (certain infarct). In practice this implies predictions are centered closer to chance level (probability 0.5), meaning the model adds limited information.

It may be seen as an objective of the inventors to obtain individualized models for the acute-follow-up association to overcome the lack of association found by averaging over a population (cf. previous references) which according to an insight made by the present inventors may be due to variations in the association patterns across patients. By estimating the cross-subject variability, a latent factor, which might not be directly observable, we can provide a model of the actual association between acute MRI and follow-up but 'cleaned' for inter-subject differences. Additionally, since this provides a handle for inter-subject differences in infarct likelihood, bounds can be established around the most probable treatment effect based on the observed population.

Hence with increasing sample size, these bounds are progressively optimized.

In the following a simple version of equation [1] is fitted, where deterministic terms linking acute modalities to risk of infarct are identical for all patients, but we include a stochastic, but patient specific term (i.e., the stochastic variable z), which offsets the overall infarct risk for individual patients.

$$\Pr(Infarct | x) = \frac{1}{1 + \exp(-z_i - \alpha_1 x_1 - \ldots - \alpha_K x_K)}$$

where $$p(z_i) = N(0, \sigma^2)$$

The random term with zero mean ensures that the effect of treatment, as well as acute MRI modalities, is adjusted for subject-specific effects. By fitting this as a random effect we simultaneously avoid overfitting, which would arise if individual models were fitted to all subjects without constraints.

Fitting this model using a Laplace approximation to the likelihood function the following effect estimates are obtained:

|  | Estimate | Std. Error | z value | Pr(>\|z\|) |  |
|---|---|---|---|---|---|
| (Intercept) | −3.900651 | 0.122091 | −31.95 | <2e−16 | *** |
| MTT | 0.116169 | 0.001384 | 83.95 | <2e−16 | *** |
| DWI | 3.217682 | 0.023244 | 138.43 | <2e−16 | *** |
| reperf.vox1 | −0.019829 | 0.158559 | −0.13 | 0.9 |  |

It is surprisingly observed that reperfusion is estimated to decrease the risk of infarct, while the isolated effects of MTT and DWI are comparable to the previous analysis. As above we can also allow the effects of MTT and DWI to change with reperfusion, which gives the following result

|  | Estimate | Std. Error | z value | Pr(>\|z\|) |  |
|---|---|---|---|---|---|
| (Intercept) | −3.051326 | 0.133502 | −22.86 | <2e−16 | *** |
| MTT | 0.043244 | 0.005815 | 7.44 | 1.04e−13 | *** |
| DWI | 2.390816 | 0.052474 | 45.56 | <2e−16 | *** |
| reperf.vox1 | −0.480028 | 0.178578 | −2.69 | 0.00719 | ** |
| MTT:DWI | 0.073944 | 0.005629 | 13.14 | <2e−16 | *** |
| MTT:reperf.vox1 | −0.021536 | 0.008543 | −2.52 | 0.01171 | * |
| DWI:reperf.vox1 | 0.432665 | 0.072255 | 5.99 | 2.12e−09 | *** |
| MTT:DWI: reperf.vox1 | 0.019729 | 0.008166 | 2.42 | 0.01569 | * |

The risk-decreasing effect of reperfusion is now clear (main effect −0.48).

Figure 9:
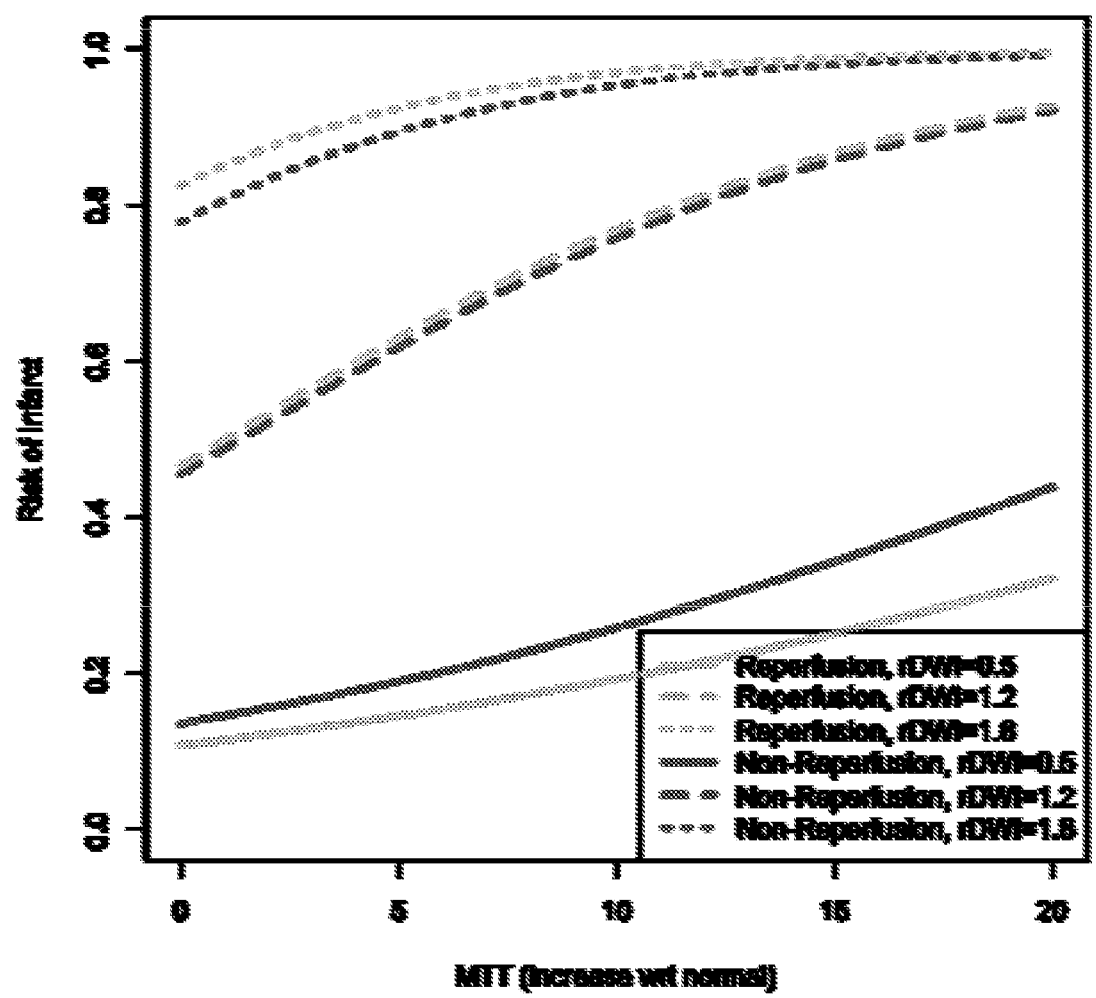
FIG. 9 shows the differential effect at various MTT and DWI combinations.

FIG. 9 shows the effect of reperfusion on infarct risk (Mixed Model) and thus shows the differential effect at various MTT and DWI combinations. As in FIGS. 5-6 the horizontal first axis represents MMT (increase with respect to normal) and the vertical second axis represents Risk of infarct.

This demonstrates that reperfusion has a beneficial effect in regions with normal DWI and prolonged MU, which is exactly the so-called penumbra region. With increasing DWI, i.e., progressive non-reversible infarct, reperfusion is indicated to be harmful, which has been hypothesized in the literature, but has not been demonstrated at the actual tissue level.

A second surprising finding with this modeling approach is that infarct probabilities are shifted away from chance level towards more certain survival/infarct.

Figure 10:
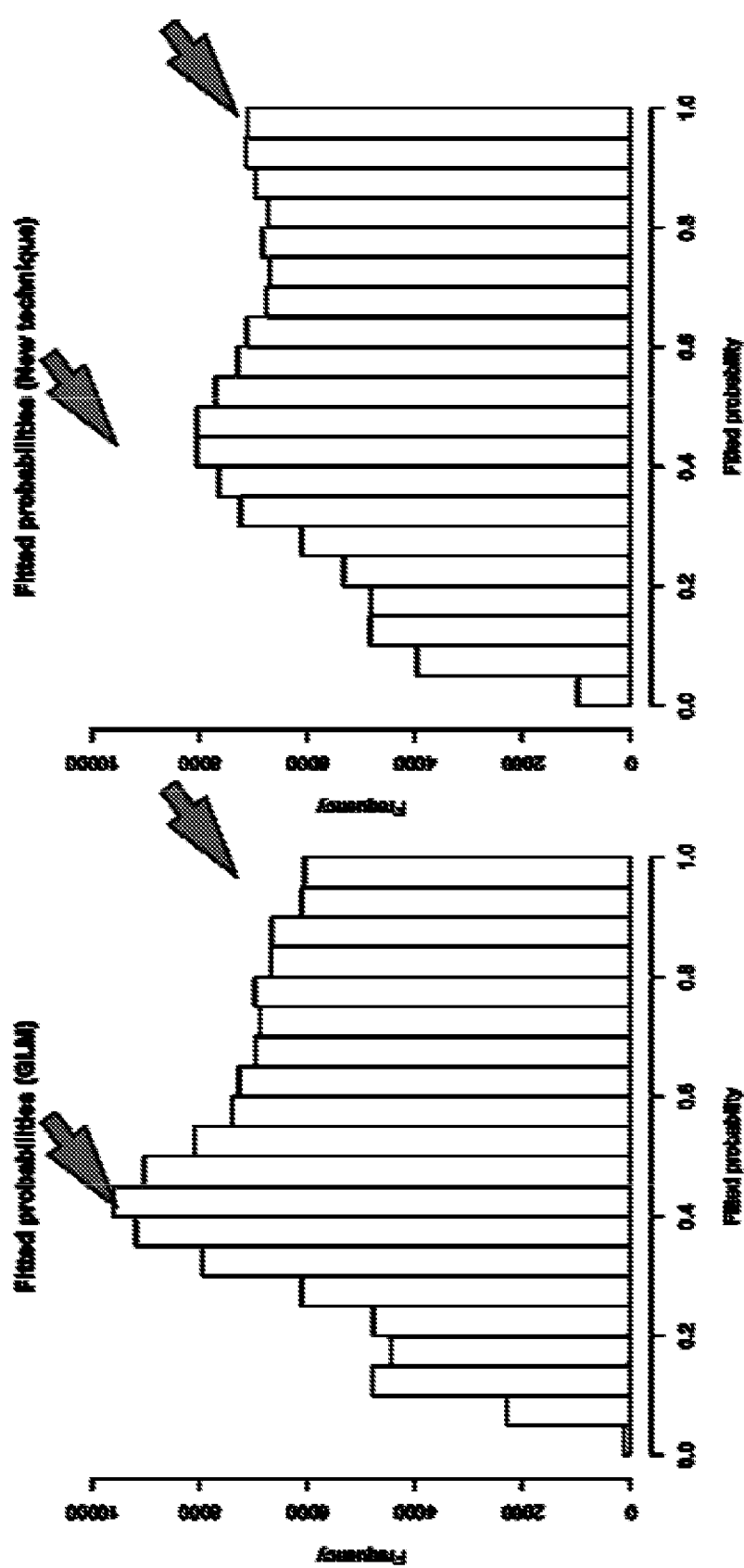
FIG. 10 demonstrates the shift away from chance level towards more certain survival/infarct by showing the histograms of fitted probabilities.

FIG. 10 demonstrates the shift away from chance level towards more certain survival/infarct by showing the histograms of fitted probabilities (the columns represent the frequencies of the fitted probabilities). The left side of FIG. 10 shows fitted probabilities as obtained with GLM. The right side of FIG. 10 shows fitted probabilities as obtained with the modeling approach according to an embodiment of the present invention. The horizontal first axis of both the left and right side graphs of FIG. 10 represents fitted probability and the vertical second axis represents frequency.

A third finding is that the GLM approach utilized in previous references either over- or underestimates infarct risk in individual patients, in comparison to embodiments of the present invention.

Figure 11:
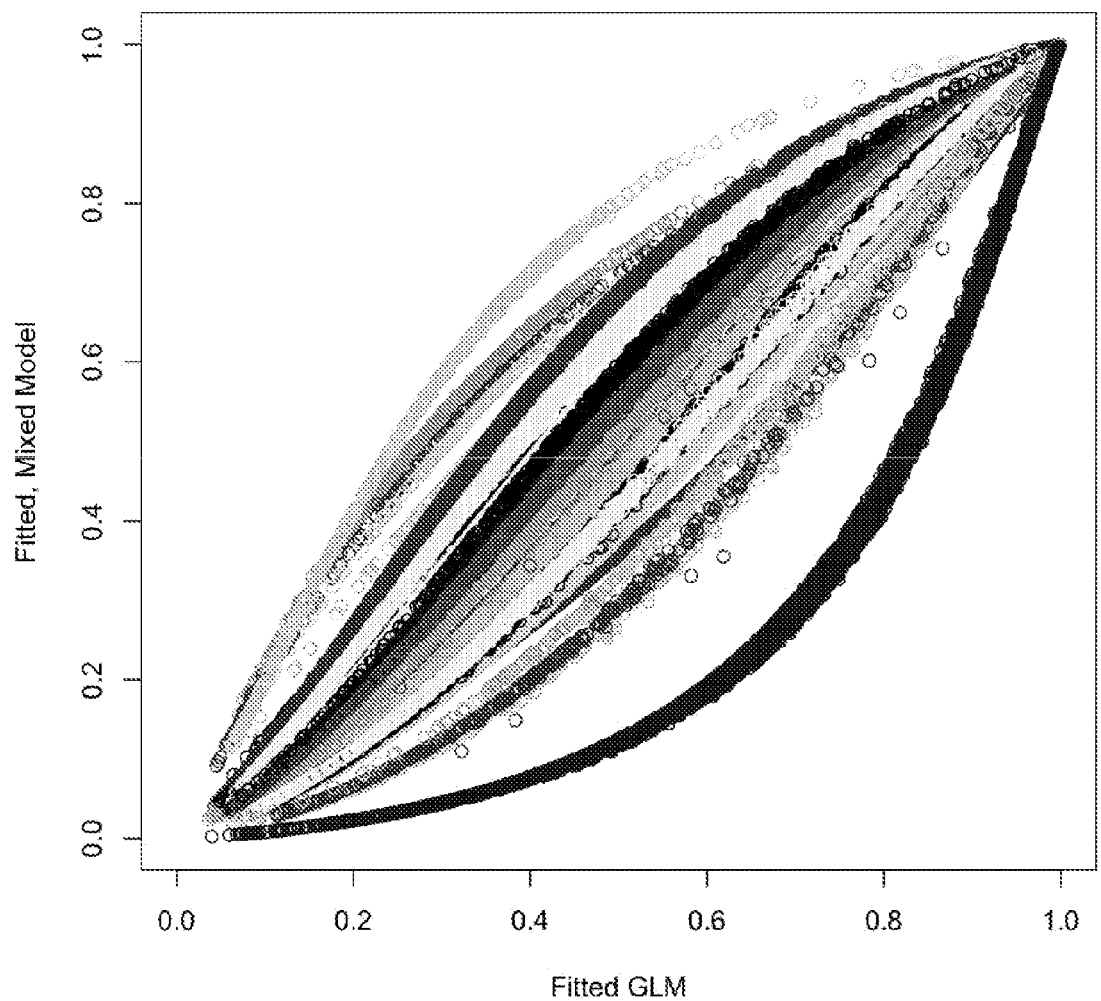
FIG. 11 shows a comparison of fitted risks for GLM and a model according to an embodiment of the invention.

FIG. 11 shows a comparison of fitted risks where the horizontal axis represents the risks fitted with GLM and the vertical axis represent risks fitted with the model according to an embodiment of the invention. Each shade of grey corresponds to a patient, and the dots represent fitted values in image voxels (note that the same shade of grey is used for multiple patients, but the trend still appears clear). The points form coherent curves, which are typically entirely below or above the identity line, suggesting that fitting with GLM as has been done in a previous reference in comparison uniformly over- or underestimates tissue risk of infarction in individual patients.

Figure 12:
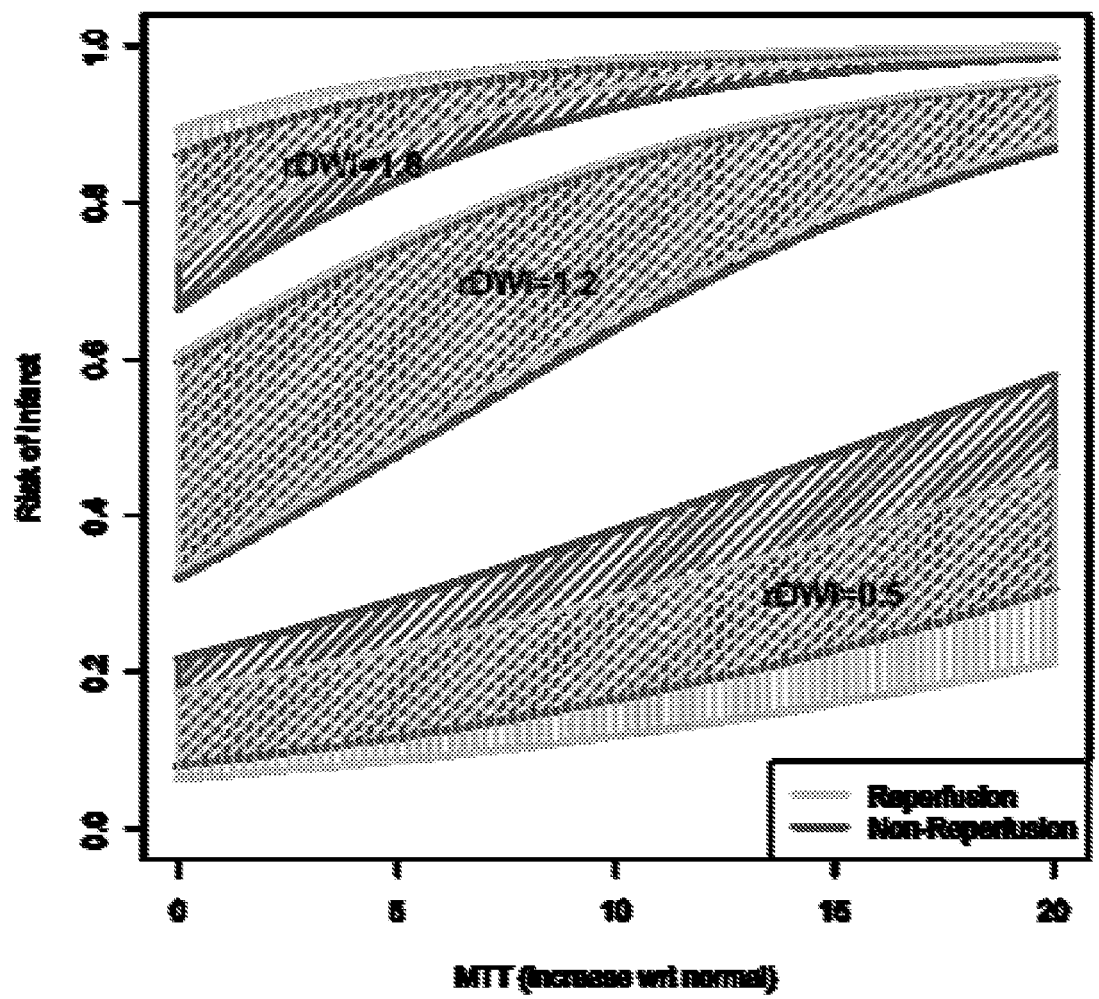
FIG. 12 shows predicted risk intervals.

A fourth finding is that methods according to embodiments of the invention may be used to generate reliable risk intervals in individuals, based on the latent, unobserved, risk variability in the population. This means that we can generate a risk interval where the individual patient's actual outcome is included with a user specified precision FIG. 12 shows predicted risk intervals where the population coverage is approximately 70%. The horizontal first axis represents MMT (increase with respect to normal) and the vertical second axis represents Risk of infarct.

Figure 13:
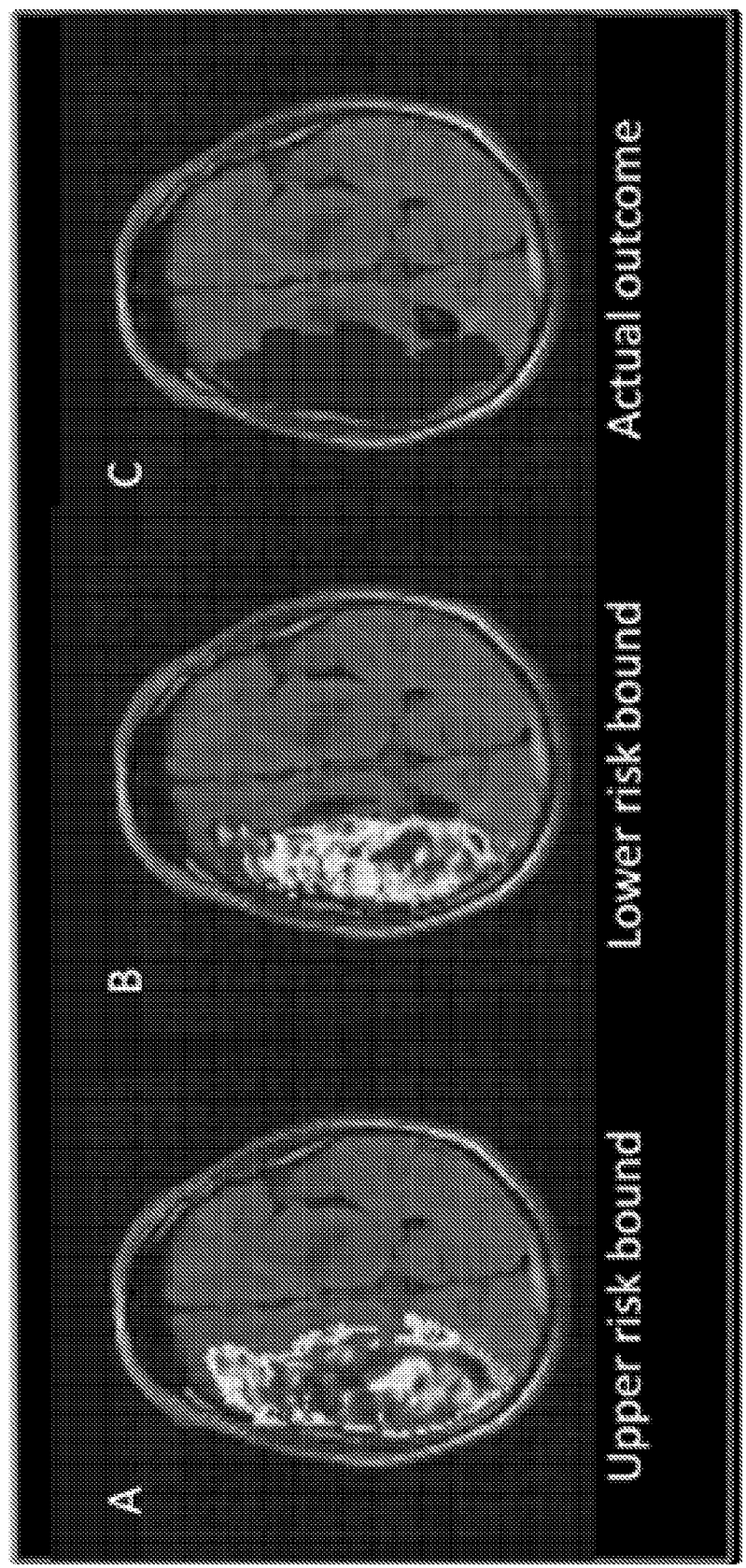
FIG. 13 illustrates the effect of the latent heterogeneity effect in a patient.

FIG. 13 illustrates the effect of the latent heterogeneity effect in a patient. The figure shows the predicted outcome for a non-reperfusing subject, using intercepts of +/−2 times the standard deviation of the population offset variability. More specifically, subfigure A shows the upper risk bound using the intercept at +2 times the standard deviation, subfigure B shows the lower risk bound using the intercept at −2 times the standard deviation, and subfigure C shows the actual outcome. Considerable differences in estimated risks are observed, although at both the upper and lower bound a large infarct is expected, in agreement with final outcome. The qualitative agreement between the upper and lower bound gives confidence in the prediction.

Tissue perfusion can be quantified using other measures than MU. Therefore it was investigated whether the same difference between prior art and the proposed technique would be consistent with the results outlined above.

Figure 14A:
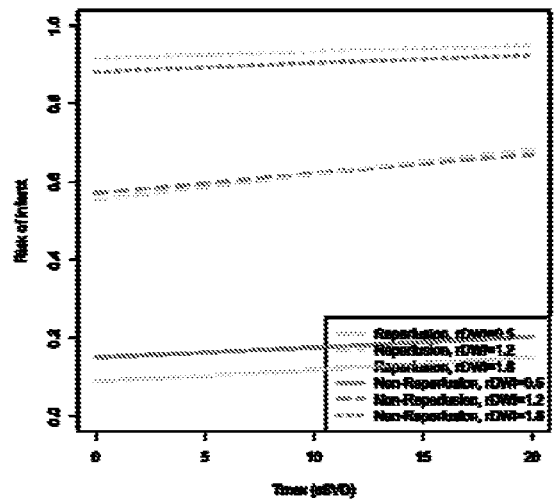
FIGS. 14-17 show the effect of reperfusion on infarct risk as a function of Tmax (sSVD), TTP capillary transit time heterogeneity (parametric) and Oxygen Extraction Fraction (parametric).
Figure 14B:
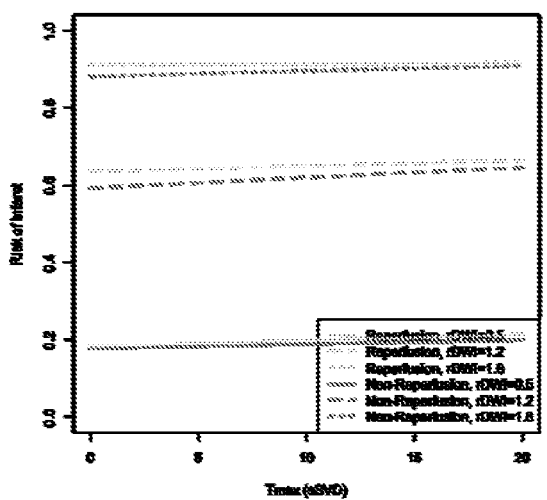

FIG. 14 shows the effect of reperfusion on infarct risk as a function of delay, Tmax (sSVD). FIG. 14A shows the effect of reperfusion on infarct risk with a Mixed Model. FIG. 14B shows the effect of reperfusion on infarct risk (logistic regression).

Figure 15A:
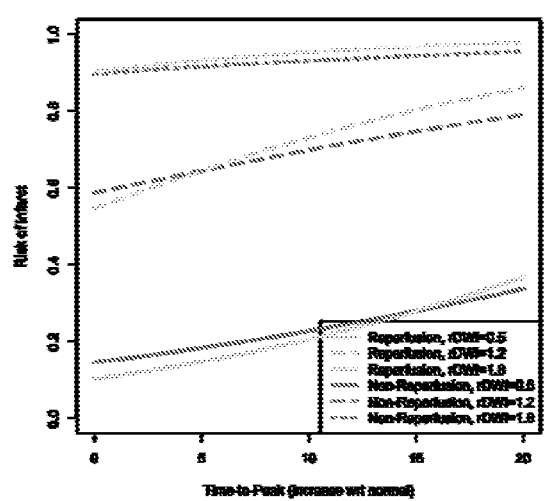
Figure 15B:
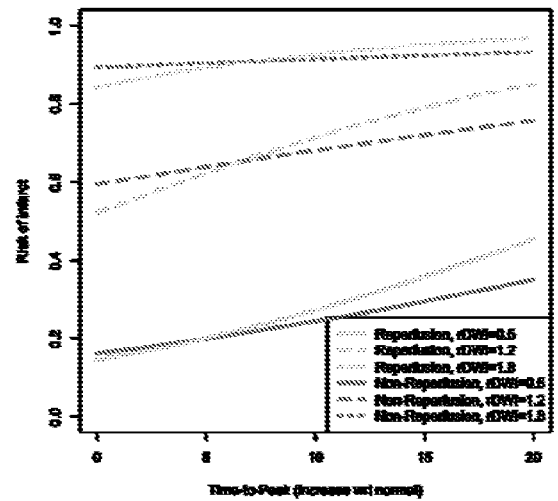

FIG. 15 shows the effect of reperfusion on infarct risk as a function of delay, TTP (model-independent). FIG. 15A shows the effect of reperfusion on infarct risk with a Mixed Model. FIG. 15B shows the effect of reperfusion on infarct risk (logistic regression).

Figure 16A:
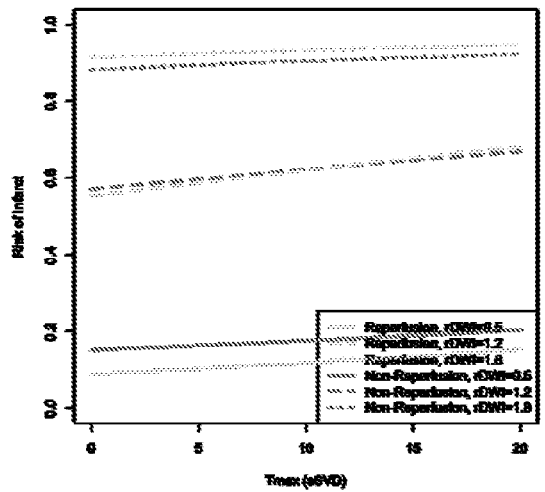
Figure 16B:
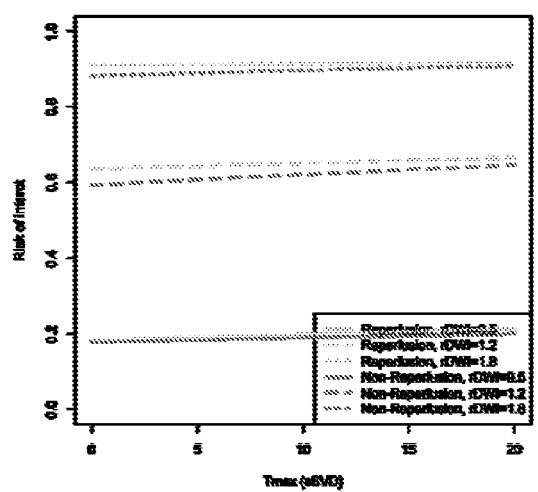

FIG. 16 shows the effect of reperfusion on infarct risk as a function of capillary transit time heterogeneity (parametric). FIG. 16A shows the effect of reperfusion on infarct risk with a Mixed Model. FIG. 16B shows the effect of reperfusion on infarct risk (logistic regression).

Figure 17A:
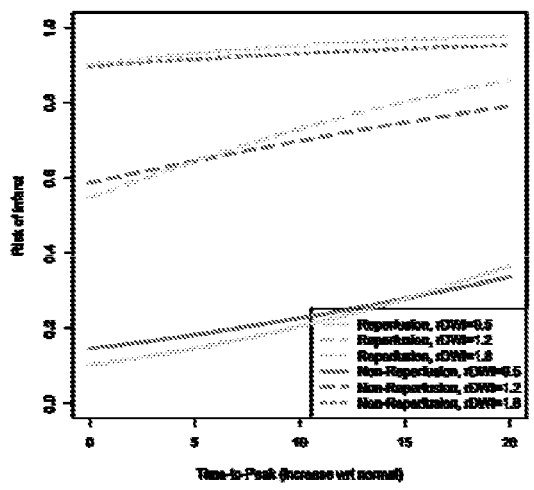
Figure 17B:
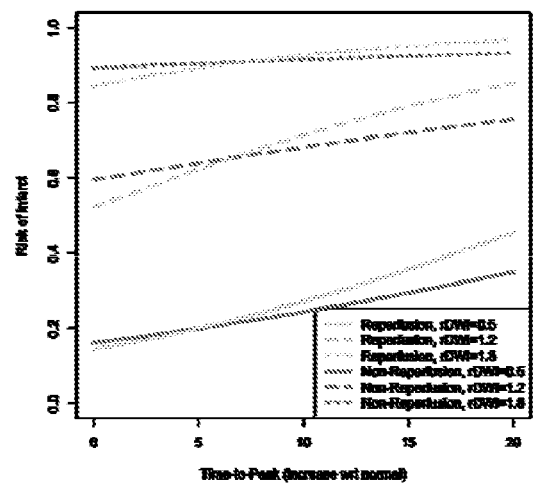

FIG. 17 shows the effect of reperfusion on infarct risk as a function of Oxygen Extraction Fraction (parametric). FIG. 17A shows the effect of reperfusion on infarct risk with a Mixed Model. FIG. 17B shows the effect of reperfusion on infarct risk (logistic regression).

FIGS. 14-17 show that this is indeed the case for a range of markers calculated using model-independent, model-dependent and parametric techniques.

The feasibility of quantifying treatment efficacy and calculating upper- and lower bounds on expected tissue outcome has been demonstrated using a simple implementation of equation [1], where the intercept term varies with subject, but is constrained by the normality assumption. However, similar results are observed with other implementations. For instance, it could be assumed that subjects can be divided into a small number of groups with identical ischemic tolerances. We can model this by assuming the stochastic variable z only takes a discrete number of values, instead of being continuous, as above. In that case the risk of infarct can be written as $$\Pr(Infarct \mid x) = \sum_{g=1}^{G} \Pr(z = z_g) \frac{1}{1 + \exp\left(-z_g - \sum_{j=1}^{K} \alpha_j x_{ji}\right)}$$

where $z_1, \ldots, z_G$ are the possible values of the stochastic variable z. For instance, with G=3 the following coefficients are obtained (where only the intercept varies):

|  | Comp. 1 | Comp. 2 | Comp. 3 |
| --- | --- | --- | --- |
| coef.MTT | 0.033834116 | 0.033834116 | 0.033834116 |
| coef.DWI | 2.401968519 | 2.401968519 | 2.401968519 |
| coef.reperf.vox1 | −0.390885397 | −0.390885397 | −0.390885397 |
| coef.MTT:DWI | 0.081028179 | 0.081028179 | 0.081028179 |
| coef.MTT:reperf.vox1 | −0.013024633 | −0.013024633 | −0.013024633 |
| coef.DWI:reperf.vox1 | 0.130016278 | 0.130016278 | 0.130016278 |
| coef.MTT: DWI:reperf.vox1 | 0.009041223 | 0.009041223 | 0.009041223 |
| coef.(Intercept) | −3.860622394 | −2.352132791 | −3.087418377 |

Similarly the coefficients for the perfusion and diffusion parameters can also be allowed to depend on the value of z, using the full generality of equation [1].

To sum up, there is provided a method for generating a risk map indicating predicted voxel-by-voxel probability of tissue infarction for a set of voxels, the method comprising the steps of, receiving for each voxel a first value (x) corresponding to a set of tissue marker values and generating the risk map, using a statistical model based on data from a group of subjects, and a stochastic variable, wherein the statistical model also comprises a second value ($z_i$), being based on the stochastic variable, such as the second value modelling non-measured values. The invention may be seen as advantageous since it acknowledges subject variability in probability of tissue infarction on a voxel-by-voxel basis by taking non-measured values into account, which in turn may enable providing more reliable estimates of probability of infarction.

The invention can be implemented by means of hardware, software, firmware or any combination of these. The invention or some of the features thereof can also be implemented as software running on one or more data processors and/or digital signal processors.

The individual elements of an embodiment of the invention may be physically, functionally and logically implemented in any suitable way such as in a single unit, in a plurality of units or as part of separate functional units. The invention may be implemented in a single unit, or be both physically and functionally distributed between different units and processors.

In exemplary embodiments E1-E19, the invention may be described as:

E1. A method for generating a risk map (106) indicating predicted voxel-by-voxel probability of tissue infarction for a set of voxels, the method comprising the steps of,
receiving (330) for each voxel a first value (x), where each first value (x) corresponds to a set of tissue marker values being representative of a quantity, such as a measurable quantity, which is representative of the corresponding voxel, and
generating (332) the risk map,
wherein the risk map is generated using a statistical model (102) based on data (104), such as data from a plurality of imaging modalities, from a group of subjects, and a stochastic variable, and wherein the statistical model receives as input for each voxel
the first value (x), and
wherein the statistical model further receives as input
a second value ($z_i$), being based on the stochastic variable, such as the second value modelling non-measured values,
and which statistical model outputs (334) the risk map.

E2. A method according to embodiment E1, wherein the first value includes Diffusion Weighted Imaging (DWI) data and/or Perfusion Weighted Imaging (PWI) data.

E3. A method according to any of the preceding embodiments, wherein the method further comprises the step of
a. Generating a plurality risk maps (106, 108, 110), where each risk map in the plurality of risk maps, corresponds to a particular value of the second value.

E4. A method according to any of the preceding embodiments, wherein the data from the group of subjects comprises an actual tissue infarction state, such as an actual tissue infarction state for a subject being represented by the first value, such as an actual follow-up tissue infarction state for a subject being represented by the first value.

E5. A method according to any one of embodiments E1-E4, wherein the statistical model (102) is given by $$Pr(\text{Infarct}|x) = G(\alpha, z, x),$$

where Pr(Infarct|x) is the risk of infarct for a voxel, the first value $x=(x_1, x_2, \ldots, x_K)$ corresponds to each of K tissue marker values for the voxel, $\alpha$ is a set of weights assigned to each of K tissue marker values, z is the stochastic variable upon which the second value $z_i$ is based, and G is a non-linear mathematical function.

E6. A method according to any one of embodiments E1-E5, wherein the statistical model (102) is given by $$Pr(\text{Infarct}|x) = G\left(\sum_{j=1}^{K} \alpha_j(z) x_j\right),$$

where Pr(Infarct|x) is the risk of infarct for a voxel, the first value $x=(x_1, x_2, \ldots, x_K)$ corresponds to each of K tissue marker values for the voxel, $\alpha(z)=(\alpha_1(z), \alpha_2(z), \ldots, \alpha_K(z))$ are weights assigned to each of K tissue marker values, z is the stochastic variable upon which the second value $z_i$ is based, and G is a mathematical function.

E7. A method according to any one of embodiments E5-E6, wherein the mathematical function G may be chosen from the set comprising:
a logistic function, $$G(t) = \frac{1}{1 + \exp(-t)}$$

a probit model, $$G(t) = \frac{1}{\sqrt{2\pi}} \int_{-\infty}^{\infty} \exp(-h^2/2) \, dh$$

a complementary log-log regression, $G(t)=1-\exp(-\exp(t))$.

E8. A method according to any of the preceding embodiments, wherein the stochastic variable z is given by a probability density function.

E9. A method according to any of the preceding embodiments, wherein the statistical model (102) is given by $$Pr(\text{Infarct}|x) = \frac{1}{1 + \exp(-z - \alpha_1 x_1 - \ldots - \alpha_K x_K)},$$

where Pr(Infarct|x) is the risk of infarct for a voxel, the first value $x=(x_1, x_2, \ldots, x_K)$ corresponds to each of K tissue marker values for the voxel, $\alpha=(\alpha_1, \alpha_2, \ldots, \alpha_K)$ are weights assigned to each of K tissue marker values, z is the stochastic variable, upon which the second value $z_i$ is based.

E10. A method according to any one of the preceding embodiments, wherein the stochastic variable z is given by $$p(z) = N(0, \sigma^2),$$

where $N(0, \sigma^2)$ is a Gaussian distribution with zero mean and non-zero standard deviation $\sigma$.

E11. A method according to any one of embodiments E1-E6, wherein the statistical model (102) is given by $$Pr(\text{Infarct}|x) = \sum_{m=1}^{M} Pr(z = z_m) \frac{1}{1 + \exp\left(-z_m - \sum_{j=1}^{K} \alpha_j x_{ji}\right)},$$

where Pr(Infarct|x) is the risk of infarct for a voxel, the first value $x=(x_1, x_2, \ldots, x_K)$ corresponds to each of K tissue marker values for the voxel, $\alpha=(\alpha_1, \alpha_2, \ldots, \alpha_K)$ are weights assigned to each of K tissue marker values, and the stochastic variable z is given by the set $(z_1, \ldots, z_M)$ of M discrete, possible values.

E12. A method according to any of the preceding embodiments, wherein the method further comprises the step of
 a. generating a plurality of risk maps (106, 108, 110), each of which is generated using said statistical model (102) based on data from a group of subjects, each group of subjects having been treated with a particular therapy.

E13. A method according to any one of the preceding embodiments, wherein the method further comprises the step of determining a volume (116) of tissue which is likely to be infarcted.

E14. A method according to any of the previous embodiments, wherein the method further comprises the steps of
 a. generating a plurality of risk maps (106, 108, 110), each of which is generated using said statistical model (102) based on data from a plurality of subjects, each plurality of subjects having been treated with a particular therapy, and
 b. for each of said risk maps, determining a volume (116, 118, 120) of tissue which is likely to be infarcted.

E15. A method according to any one of embodiments E13-E14, wherein the volume of tissue which is likely to be infarcted is determined by calculating the sum, over all voxels, of the product between the volume of each voxel multiplied by the probability of infarct for said voxel.

E16. A method according to any of the previous embodiments, wherein the method further comprises the steps of
 receiving patient related information, such as clinical findings.

E17. A system (222) comprising a processor (224) arranged for carrying out the method according to any one of the preceding embodiments.

E18. A system (222) according to embodiment E17, wherein the system furthermore comprises an apparatus (226) arranged for obtaining one or more first values, such as a nuclear magnetic resonance scanner.

E19. A computer program product enabled to carry out the method according to any one of embodiments E1-E16.

In further exemplary embodiments E20-E26, there is presented

E20. A method for generating a risk map (106) indicating predicted voxel-by-voxel probability of tissue infarction for a set of voxels, the method comprising the steps of,
 receiving (330) for each voxel a first value (x), where each first value (x) corresponds to a set of tissue marker values being representative of a quantity, such as a measurable quantity, which is representative of the corresponding voxel, and
 generating (332) the risk map,
 wherein the risk map is generated using a statistical model (102) based on data (104), such as data from a plurality of imaging modalities, from a group of subjects, and wherein the statistical model receives as input for each voxel
 the first value (x),
 and which statistical model outputs (334) the risk map.

E21. A method according to embodiment E20, wherein the method further comprises
 receiving a background map based on follow-up images for a secondary group of subjects, said background map being indicative of infarct likelihood as a function of spatial position,
 and wherein the risk map is based on the background map.

E22. A method according to embodiment E21, wherein the risk map is based on the background map by having the statistical model being based on data (104) from a group of subjects and a stochastic variable and the background map.

E23. A method according to embodiment E21, wherein the risk map is based on the background map by having the statistical model based on data (104) from a group of subjects and a stochastic variable output the risk map, and wherein said risk map is subsequently amended based on the background map.

E24. A system (222) comprising a processor (224) arranged for carrying out the method according to any one of the embodiments E20-E23.

E25. A system (222) according to embodiment E24, wherein the system furthermore comprises an apparatus (226) arranged for obtaining one or more first values, such as a nuclear magnetic resonance scanner.

E26. A computer program product enabled to carry out the method according to any one of the embodiments E20-E23.

Although the present invention has been described in connection with the specified embodiments, it should not be construed as being in any way limited to the presented examples. The scope of the present invention is set out by the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims or embodiments, may possibly be advantageously combined, and the mentioning of these features in different claims or embodiments does not exclude that a combination of features is not possible and advantageous.

The invention claimed is:

1. A method for generating a risk map indicating predicted voxel-by-voxel probability of tissue infarction for a set of voxels, the method comprising,
 receiving for each voxel a first value (x), where each first value (x) corresponds to a set of tissue marker values being representative of a quantity, which is representative of the corresponding voxel, and
 generating the risk map,
 wherein the risk map is generated using a statistical model based on data, from a group of subjects, and a stochastic variable, and wherein the statistical model receives as input for each voxel
 the first value (x), and
 wherein the statistical model further receives as input
 a second value ($z_i$), being based on the stochastic variable, and which statistical model outputs the risk map.

2. The method according to claim 1, wherein the second value is chosen as a mean value of the stochastic variable.

3. The method according to claim 1, wherein the first value includes Diffusion Weighted Imaging data and/or Perfusion Weighted Imaging data.

4. The method according to claim 1, wherein the method further comprises generating a plurality of risk maps, where each risk map in the plurality of risk maps, corresponds to a particular value of the second value.

5. The method according to claim 1, wherein the method further comprises
receiving a background map based on follow-up images for a secondary group of subjects, said background map being indicative of infarct likelihood as a function of spatial position,
and wherein the risk map is generated using the background map.

6. The method according to claim 5, wherein the risk map is based on the background map by having the statistical model being based on said data from a group of subjects and said stochastic variable and the background map; or,
wherein the risk map is based on the background map by having the statistical model based on said data from a group of subjects and the stochastic variable output the risk map, and wherein said risk map is subsequently modified based on the background map.

7. The method according to claim 1, wherein the statistical model is given by:

$$Pr(\text{Infarct}|x) = G(\alpha, z, x),$$

where Pr(Infarct|x) is the risk of infarct for a voxel, the first value $x=(x_1, x_2, \ldots, x_K)$ corresponds to each of K tissue marker values for the voxel, $\alpha$ is a set of weights assigned to each of K tissue marker values, z is the stochastic variable upon which the second value $z_i$ is based, and G is a non-linear mathematical function.

8. The method according to claim 7, wherein a subject specific tendency of tissue to infarct is modelled with the stochastic variable.

9. The method according to claim 7, wherein the mathematical function G is selected from the group consisting of:
a logistic function,
a probit function, and
a complementary log-log regression.

10. The method according to claim 7, wherein the stochastic variable z is given by a probability density function.

11. The method according to claim 1, wherein the statistical model is given by:

$$Pr(\text{Infarct}|x) = G\left(\sum_{j=1}^{K} \alpha_j(z) x_j\right),$$

where Pr(Infarct|x) is the risk of infarct for a voxel, the first value $x=(x_1, x_2, \ldots, x_K)$ corresponds to each of K tissue marker values for the voxel, $\alpha(z)=(\alpha_1(z), \alpha_2(z), \ldots, \alpha_K(z))$ are weights assigned to each of K tissue marker values, z is the stochastic variable upon which the second value $z_i$ is based, and G is a mathematical function.

12. The method according to claim 1, wherein the statistical model is given by:

$$Pr(\text{Infarct}|x) = \frac{1}{1+\exp(-z-\alpha_1 x_1 - \ldots - \alpha_K x_K)},$$

where Pr(Infarct|x) is the risk of infarct for a voxel, the first value $x=(x_1, x_2, \ldots, x_K)$ corresponds to each of K tissue marker values for the voxel, $\alpha=(\alpha_1, \alpha_2, \ldots, \alpha_K)$ are weights assigned to each of K tissue marker values, and z is the stochastic variable, upon which the second value $z_i$ is based.

13. The method according to claim 12, wherein the stochastic variable z is given by:

$$p(z)=N(0,\sigma^{-2}),$$

where $N(0,\sigma^2)$ is a Gaussian distribution with zero mean and non-zero standard deviation $\sigma$.

14. The method according to claim 13, said method further comprising making of the statistical model, and wherein said making of the statistical model comprises fitting the risk of infarct Pr(Infarct|x),
and wherein
adjustment for subject-specific effects is enabled by fitting this as a random effect parameterized as the stochastic variable z.

15. The method according to claim 1, wherein the statistical model is given by:

$$Pr(\text{Infarct}|x) = \sum_{m=1}^{M} Pr(z=z_m) \frac{1}{1+\exp\left(-z_m - \sum_{j=1}^{K} \alpha_j x_{ji}\right)},$$

where Pr(Infarct|x) is the risk of infarct for a voxel, the first value $x=(x_1, x_2, \ldots, x_K)$ corresponds to each of K tissue marker values for the voxel, $\alpha=(\alpha_1, \alpha_2, \ldots, \alpha_K)$ are weights assigned to each of K tissue marker values, and the stochastic variable z is given by the set $(z_1, \ldots, z_M)$ of M discrete, possible values.

16. The method according to claim 1, wherein the method further comprises generating a plurality of risk maps, each of which is generated using said statistical model based on data from a group of subjects, each group of subjects having been treated with a particular therapy.

17. The method according to claim 1, wherein the method further comprises determining a volume of tissue, which is likely to be infarcted, wherein the volume of tissue, which is likely to be infarcted, is determined by calculating a sum, over all voxels, of a product between the volume of each voxel multiplied by the probability of infarct for said voxel.

18. A system comprising a processor arranged for carrying out the method according to claim 1.

19. The system according to claim 18, wherein the system further comprises an apparatus arranged for obtaining one or more first values.

20. A non-transitory computer-readable storage medium storing a computer program product enabled to carry out the method according to claim 1.

* * * * *